United States Patent [19]

Mayer et al.

[11] Patent Number: 4,911,230
[45] Date of Patent: Mar. 27, 1990

[54] TEST CHAMBER PROVIDING RAPID CHANGES OF CLIMATE TEMPERATURE

[75] Inventors: Xaver Mayer, Grosselfingen; Hermann Ruoss; Werner Hezel, both of Balingen, all of Fed. Rep. of Germany

[73] Assignee: Heraeus-Vötsch GmbH, Hanau, Fed. Rep. of Germany

[21] Appl. No.: 371,660

[22] Filed: Jun. 16, 1989

Related U.S. Application Data

[62] Division of Ser. No. 144,805, Jan. 15, 1988, abandoned.

[30] Foreign Application Priority Data

Jan. 15, 1987 [DE] Fed. Rep. of Germany ....... 3700976

[51] Int. Cl.$^4$ ..................... F25B 29/00; F28D 15/02
[52] U.S. Cl. ..................... 165/48.1; 165/61; 165/63; 165/64; 165/104.21; 62/333
[58] Field of Search ............... 62/333; 165/104.21, 165/61, 63, 48, 58, 64; 126/4

[56] References Cited

U.S. PATENT DOCUMENTS

| | | | |
|---|---|---|---|
| 2,022,764 | 12/1935 | Gibson et al. | 62/333 |
| 2,040,744 | 5/1936 | Hull | 62/333 |
| 2,510,952 | 6/1950 | Brewster | 165/63 |
| 2,555,012 | 5/1951 | Spofford | 165/63 |
| 3,603,379 | 9/1971 | Leonard, Jr. | 62/333 |
| 4,340,111 | 7/1982 | Sbala | 165/61 |

FOREIGN PATENT DOCUMENTS 1698104 3/1972 Fed. Rep. of Germany .
2721862 11/1978 Fed. Rep. of Germany .

Primary Examiner—Albert W. Davis, Jr.
Attorney, Agent, or Firm—Frishauf, Holtz, Goodman & Woodward

[57] ABSTRACT

The heat exchanger located in an air-conditioning room adjourning the test room of a climatic test chamber for testing equipment and devices for their resistance to extremes of climate is equipped for producing rapid changes of test chamber air temperature towards extremes of cold and heat by means of a so called "tempering" heat transfer medium which boils or condenses in the heat exchanger in the air-conditioning room. The heat transfer loop of the tempering medium is designed to withstand pressures from a low value such a 0.1 bar to a high value such as 20 bar in order that the boiling point of the tempering medium may automatically rise and fall with the air temperature of the testing room while heat is transferred in one direction or the other in great quantity through a low temperature gradient at the boiling point temperature. For cooling, a condensate separator is included in the tempering medium loop and is cooled by the cooling loop of another cooling medium. For heating, a vaporizer is included in the circulation loop of the tempering medium and is heated by a built-in heater. Both for cooling and heating the tempering medium moves around its loop by gravity feed of the condensate, making pumps unnecessary and likewise all but a minimum of valves.

10 Claims, 3 Drawing Sheets

FIG. 3.
FIG. 4.
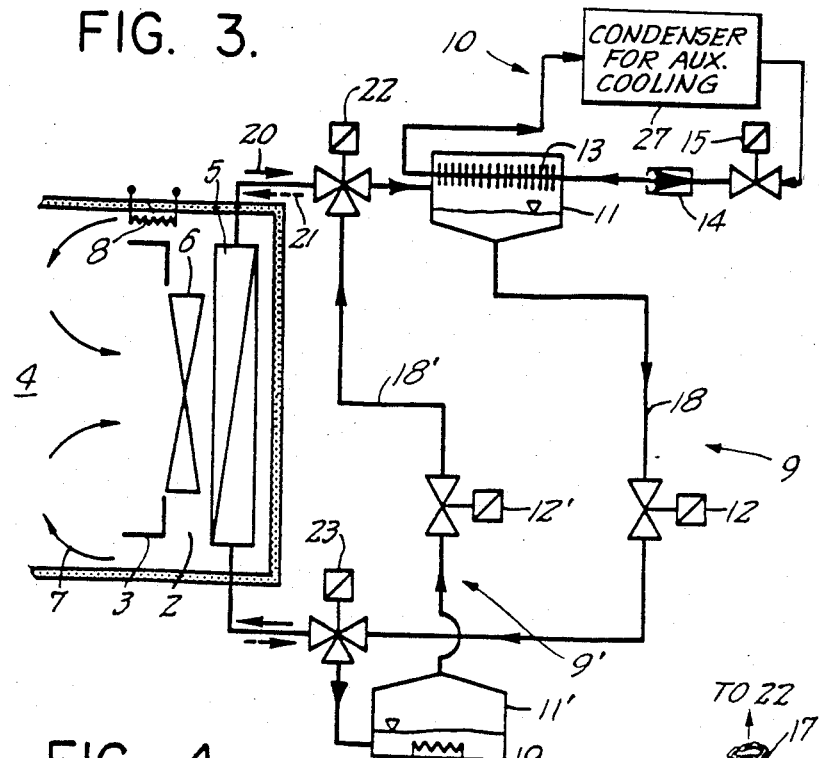
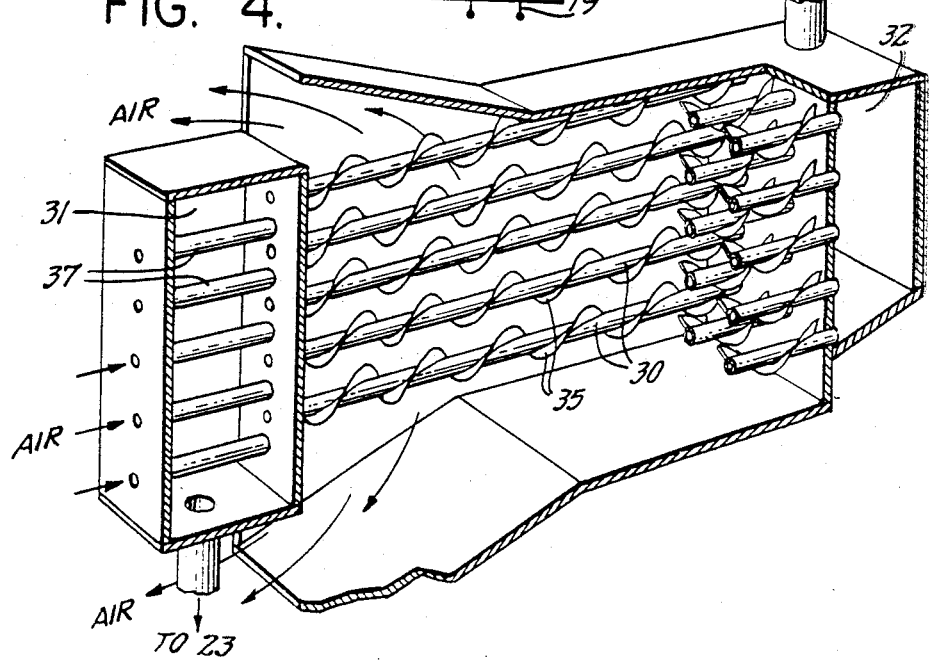

TEST CHAMBER PROVIDING RAPID CHANGES OF CLIMATE TEMPERATURE

This application is a division of application Ser. No. 144,805, filed Jan. 15, 1988, now abandoned.

This invention concerns a climatic test chamber having a test room and an adjoining air-conditioning room in which a heat exchanger is provided and connected for circulation of a transfer medium of the kind that is sometimes called a tempering medium. The term "tempering" is here used to designate the production of rapid changes of temperature such as might be used for tempering articles of certain kinds, rather than to designate moderation. "Air-conditioning" is used herein to include both cooling the air and heating the air of the test chamber to extreme limits of a climate test, with capability of doing so rapidly. In order to produce low test room temperature, the tempering system includes an evaporator for cooling the tempering medium.

Climatic test chambers of known types are described in German published patent applications (AS) 1 698 104, (OS) 27 21 862 and (OS) 34 05 584 and in German Pat. No. 19 49 001.

In such test chambers it is necessary to obtain rapid changes of temperature that can take place within a temperature range, for example, from 180° C. down to −80° C. For such tempering tests various systems are known. For example, indirect tempering systems are used in which heating and cooling continuously affect the test room air by means of interposed separate heat carriers (e.g. brines, oil or air). For heat exchange between the test room air and the intermediate heat transfer medium, heat exchangers are used that are typically installed either in an air conditioning room or in the walls of the test room. For rapid cooling or heating of the test room air, a large effective heat exchanger surface is necessary. Such tempering systems have up to now been very useful in application, but they require much maintenance effort for the pumps and valves necessary for circulation of the tempering medium.

SUMMARY OF THE INVENTION

It is an object of the present invention to provide a climatic test chamber in which rapid temperature changes within a large tempering temperature range can be obtained both in cooling and in heating up while at the same time movable parts such as pumps, become unnecessary and valves are reduced to a minimum.

Briefly, a tempering medium is used having a boiling point that varies over substantially the desired tempering temperature range. The tempering medium is generally referred to herein as the first fluid heat exchange medium of the rapid tempering system of the invention It is used in a circulation loop, such as a substantially closed circulation loop, in which the pressure rises as the test chamber air temperature increases and falls as the test chamber temmperature falls, so that this first fluid medium can continuously operate to transfer heat at its boiling point. For rapid cooling, the heat exchanger in the air-conditioning room operates as a vaporizer and for rapid heating it operates as a condenser. In the first case an additional condenser, cooled by the evaporator of a second fluid heat exchange medium, is provided in the tempering system and in the second case in additional vaporizer is provided in the circulation system of the tempering medium. In both cases, the tempering medium circulates by virtue of gravity feed of the separated condensate to the equipment serving as the vaporizer.

For the case of producing rapid cooling, the condenser is located relatively high compared to the heat exchanger, so that the condensate can flow to the lower flow connection of the heat exchanger and can be distributed upward therein by gravity for vaporization therein. In the case of rapid heating, the vaporizer, which may be made the same way as the condenser except for the provision of heating means for the condensate instead of cooling means for the vapor, must be placed below the lower tempering medium connection of the heat exchanger in the air conditioning room in order to provide gravity feed.

It is possible to provide climatic test chambers according to the invention in which either rapid heating or rapid cooling of the test chamber air, can be selectively performed even in quick succession in accordance with the invention.

A "climate cell" constituted as above outlined can have a very simple construction. When a tempering fluid medium as above defined as used, large, quantities of heat can be transferred with the smallest of temperature gradients at the heat exchanger in the air-conditioning room. No components with parts that wear, as for example pumps, are necessary for heat transport by the circulation of fluid medium, so that the equipment of the climatic test chamber in accordance with the invention provides a system that is easy to maintain.

Switching valve means can be provided for change over from heating to cooling, having their respective common path ports connected to opposite ends of the exchanger in the air-conditioning room. These switch between cooling and heating paths of the tempering medium. These may also perform the shut-off functions as well, if desired, while individual control valves may be used for controlling the rate of heating or cooling.

Preferably a control valves are respectively interposed in the cooling and heating paths of the circulation loop of the tempering medium respectively after or before its passage through the heat exchanger in the air-conditioning room.

These control valves should be able to operate at least as a shut-off device but preferably they also permits adjustment of the flow rate of the tempering medium.

One can conviently be interposed between an exteranal condenser and the condensate inlet of the heat exchanger in the air-conditioning room for the case of a rapid cooling system and another for the case of a rapid heating system, between the outlet of the vaporizer and the upper connection for inlet of vapor into the heat exchanger in the air conditioning room. On the other hand, it might be desirable in some cases for the control valves to be in the condensate flow conduit in both cases.

In a case in which both rapid heating and rapid cooling are provided, switching valve means can be provided for change over from heating to cooling, having their respective common path ports connected to opposite ends of the exchanger in the air-conditioning room. These may also perform the shut-off functions as well, if desired, while individual control valves may be used for controlling the rate of heating or cooling.

For rapid heating, the vaporizer for the tempering medium, which as already mentioned can have the same construction as a condenser except for the provision of a condensate heater instead of a vapor cooler, preferably has an electrical resistance heater for vaporizing the condensate. The regulation of the circulation of the tempering medium can be performed on the one hand by control of the power of the heater just mentioned and on the other hand by a supplemental valve, preferably a magnetic valve, which is interposed in the piping leading the gaseous phase of the tempering medium to the upper connection of the heat exchanger in the air-conditioning room.

For the heat exchanger in the air-conditioning room it has been found useful to use a construction providing a multiplicity of horizontally positioned tubes connected by a common manifold to the bottom of the heat exchanger for receiving the liquid phase of the tempering medium. Their other ends lead into a common duct leading to an upper connection for the gas phase. This is particularly useful when the heat exchanger operates as a vaporizer in which the liquid phase boils. The tubes may be slightly inclined at an angle up to about 5 degrees to permit a certain amount of the liquid phase to be present continuously in each tube. In this type of a heat exchanger the liquid phase goes over into the vapor phase in a very short time.

For the evaporator used for cooling the condenser outside of the air-conditioning room by means of a second fluid heat transfer medium, serpentine tubes, especially finned tubes or tube and sheet heat exchangers, have been found advantageous. A cooling medium of halogen-substituted hydrocarbon containing at least one atom of fluorine per molecule is preferably used as the cooling means for a temperature range from $-20°$ C. up to $+100°$ C.

BRIEF DESCRIPTION OF THE DRAWINGS

The invention is further described by way of illustrative example with reference to the annexed drawing, in which:

FIG. 3 is a schematic representation of a tempering system according to the invention for both cooling and heating the test chamber air;

FIG. 4 is a schematic cross-section of an illustrative form of construction of the heat exchanger of the air-conditioning room especially for the case of FIG. 1, and FIGS. 5 and 6 are diagrams showing the condenser 11 of FIGS. 1 and 3 equipped with different types of evaporators for cooling the condenser by circulation of a second fluid heat transfer medium.

DESCRIPTION OF THE ILLUSTRATED EMBODIMENTS

Figure 1:
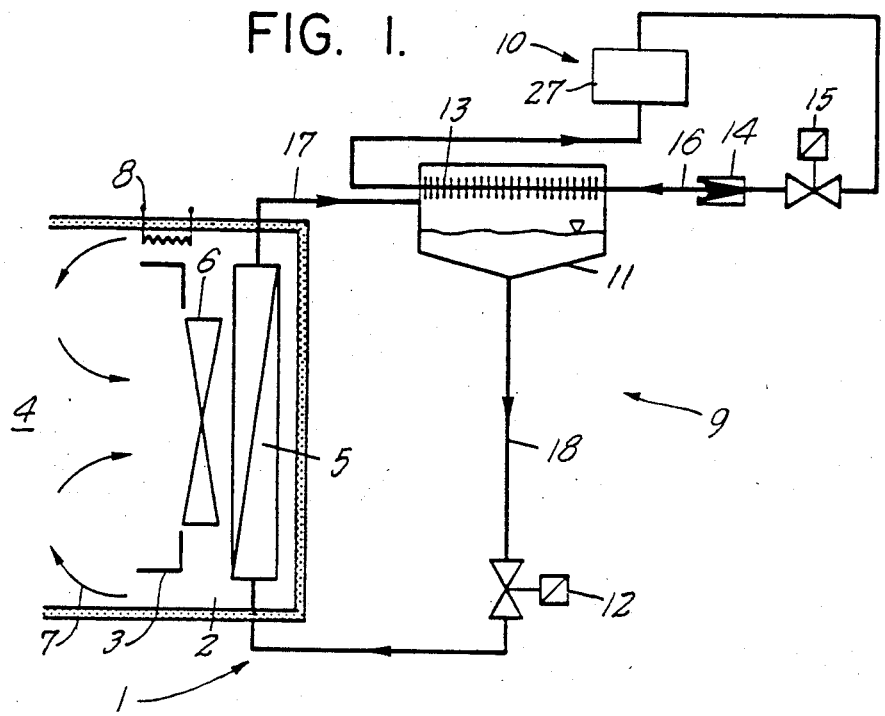
FIG. 1 is a schematic representation of a tempering system according to the invention for cooling the test chamber air.

FIG. 1 shows a portion of a climatic test chamber 1 showing only the portion of the test room 4 which adjoins the air conditioning room 2 which is separated from the test room by partition walls 3. The heat exchanger 5 and a blower 6 are located in the air-conditioning room 2, the blower 6 receiving air from the test room 4 through a large aperture in the partition 3 to blow it past the heat exchanger 5 and back into the test chamber 4 through passages near the walls as shown by the arrows in FIG. 1 illustrating the air circulation.

In the climatic test chamber illustrated in FIG. 1 heating and cooling of the test chamber are performed by two separate systems. A heating the heating body 8 is disposed in the upper region of the air-conditioning room 2, by the operation of which air flowing out of the air-conditioning room is heated. For cooling of the test room air, an indirect tempering system is provided composed of a first tempering system 9 and a second tempering system 10. The first tempering system 9 includes, in addition to the heat exchanger 5, a condenser 11 and a shut-off device 12. The second tempering system 10 includes an evaporator 13 that is a part of the condenser 11, an expansion valve 14 and a control valve 15 as well as additional equipment 27 including a condenser not separately shown.

A boiling liquid fills the first tempering system 9. the second tempering system 10 provides a circulating flow of a suitable second cooling medium, which may be of the same kind as used in the system 9 but is not necessarily such. This second cooling medium is led through the vaporizer supply line 16 to the vaporizer 13, so that the latter, which in the illustrated case is shown (FIG. 1) as a finned tube, is kept cooled to a low temperature such as, for example, $-20°$ C.

Figure 5:
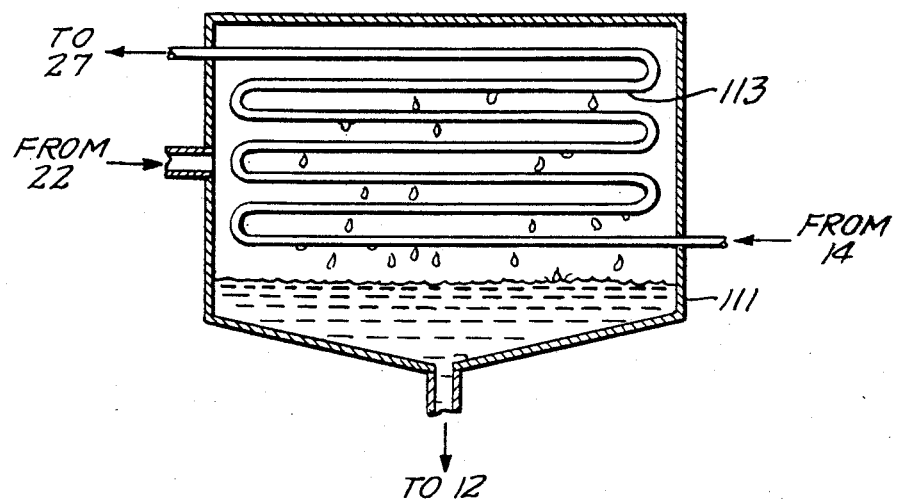
Figure 6:
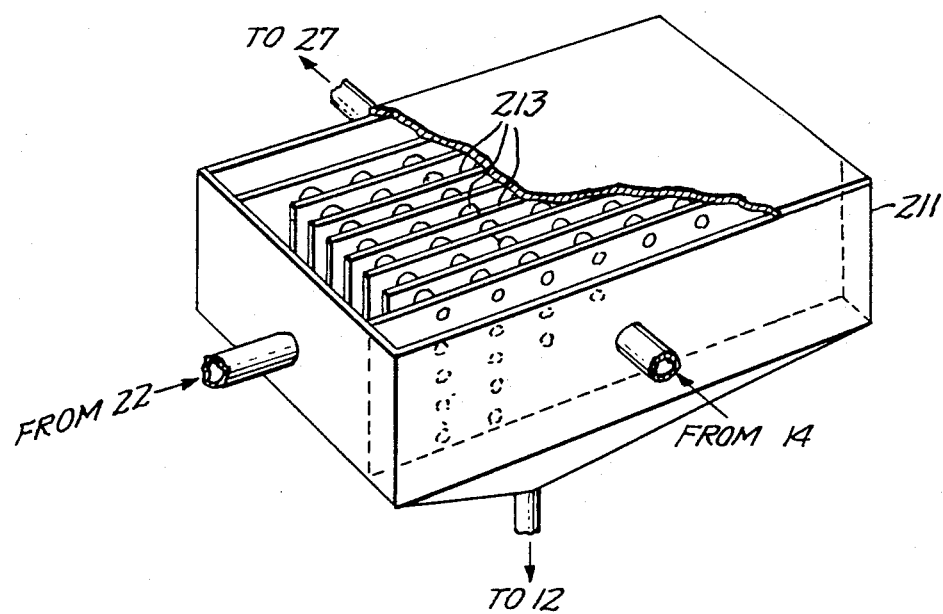

FIGS. 5 and 6 respectively show that the evaporator 13 of the condenser 11 could be replaced by the serpentine tube evaporator 113 of the condenser 111 of FIG. 5 or by the sheet and tube evaporator 213 of the condenser 211 of FIG. 6.

The gas phase of the boiling tempering liquid let out through the line 17 from the top of the heat exchanger 5 condenses on this vaporizer (the finned tube 13) of the second tempering system 10 and drips into the lower region of the endenser 11, the deepest portion of which is connected with a supply line 18 that leads the liquid phase of the first fluid medium through the shut-off device 12 to the inlet at the bottom of the heat exchanger 5. The liquid then vaporizes again in the heat exchanger 5 by means of the quantity of heat which is removed from the air sucked out of the test room 4 by means of the blower 6. The vapor components of the boiling liquid flow through a riser duct (not shown in FIG. 1) in the heat exchanger 5 and then through the line 17 into the condenser 11, where condensation takes place.

In this tempering system only small temperature gradient is found between the temperature of the air of the air-conditioning room and the temperature in the supply line 18 to the heat exchanger 5 and likewise between these temperatures and the temperature of the line 17 leading to the condenser 11. Taking account of such a small temperature gradient the heat exchanger 5 should have the greatest possible effective surface, for which reason it occupies the entire height of a large portion of the air-conditioning room in the illustrated example. Since the entire vaporization heat of the boiling liquid is available for heat transfer, very large quantities of heat can be transported over small temperatures gradients. By the use of a suitable heat transfer medium a large temperature range can be covered by such a heat transfer operation. For example, the circulation loop of the illustrated example was designed for an overpressure of about 20 bar and the material R11 (designation for trichlorfluoromethane in German standard DIN 8962), was used as the heat transfer medium. In operation a temperature range from $-20°$ C. to $+150°$ C. could be obtained corresponding to a pressure range from about 0.15 bar to 20 bar. While the shut-off device 12 in the supply line to the heat exchanger 5 serves merely for decoupling the tempering system 9 from the heat exchanger, the actual tempering effect by the supply of cooling medium to the vaporizer 13 is adjustable by means of the expansion valve 14 and the control valve 15.

Apart from the shut-off device 12 there are no movable parts subject to substantial wear in the tempering system 9, so that this system is distinguished for its ease of maintenance.

FIG. 4 shows schematically a preferred form of heater exchanger 5 for the system of FIG. 1, in a vertical cross-section passing through the respective axes of the middle set or stack of the tubes 30. The tubes 30 are arrayed in horizontal rows as well as in vertical stacks.

The many horizontally running tubes 30 are provided which are connected, with rising direction from their inlet to their outlet, with the supply line 18 for the liquid phase of the tempering medium through a connection head 31. These essentially horizontal tubes are mounted with a slight angle of rise. Their open ends lead into a vertical riser duct 32 that is connected at the top to the line 17 leading to the condensate separator 11. Air enters the heat exchanger through short tubes 37 that pass through the connection head 31 to lead air to the space between the tubes 30 and between the header 31 and the riser 32. It escapes at top and bottom in order to circulate as shown in FIG. 1. Such a heat exchanger is distinguished by its high efficiency. Its effective surface is increased by the fact that the individual tubes are surrounded by a fin-like rib element 35, shown in FIG. 4 as having a helical shape, although serpentine or other shapes are usable.

In the case of the tempering system 9' shown in FIG. 2, the device 11' that resembles in its illustration the condenser of FIG. 1 operates as a vaporizer and is located at a level below that of the heat exchanger 5. In the lower region of the device 11', in which there is located the liquid phase of the boiling liquid, a heating body 19 is provided by which the liquid can be vaporized. The vapor phase is supplied over the line 18', in which the shut-off device 12' is interposed, for supply to the upper end of the heat exchanger 5, in which this gaseous phase is condensed as a result of the warming of the heat exchanger 5 by the air blown on the latter by the blower 6. The condensate then flows down through the line 17' and back into the device 11'. Heating of the test room air can on the one hand be adjusted by the power supplied to the heater 19 and on the other hand by operation of the device 12', which in this case is not a shut-off device but also a control valve. The device 12' then can control the flow of gas for controlling the rate of heating of the test chamber air.

Figure 2:
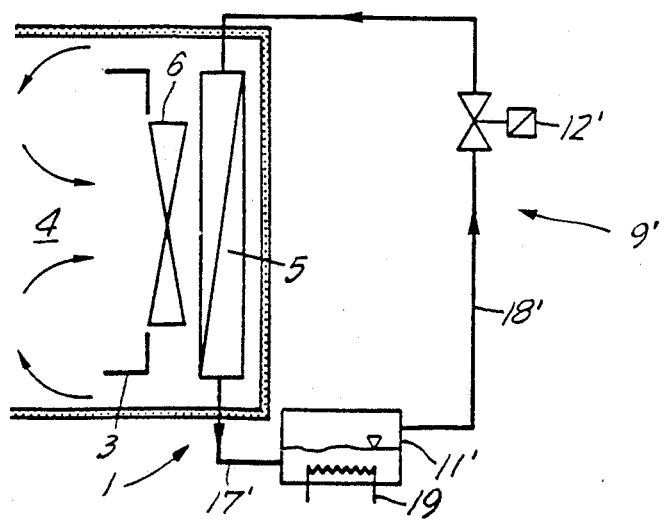
FIG. 2 is a schematic representation of a tempering system according to the invention for heating the test chamber air.

FIG. 3 shows an embodiment of the invention in which the features of FIGS. 1 and 2 are combined so that the climatic test chamber can be both rapidly heated and rapidly cooled, selectively, in accordance with the invention.

Reference is made to FIGS. 1 and 2 for the manner for operation of the devices 11 and 11' shown in FIG. 3 which correspond to the devices 11 and 11' shown respectively in FIGS. 1 and 2. The cooling operation is performed by means of the condenser 11, the direction of flow of the boiling liquid and its vapor being indicated by the solid arrows 20, whereas the direction of flow of this first tempering medium during a heating operation by means of the device 11' is shown by the broken line arrows 21. Switching over of the tempering from cooling to heating or vice versa is performed by simultaneous switching over of the switching valve means 22 and 23. These switching valve means can in each case simply be three-port two-path valves with their common path ports respectively connected to the ends of the heat exchanger 5 or they may each be a combination of two or more valves having the same effect, or the like. The cooling path 9 makes use of a first-path port of the switching valve means 22 and a first-path port of the switching valve means 23, while the heating path 9' makes use of a second-path port of the switching valve means 22 and a second-path port of the switching path means 23. If the valve 12 is a control valve as well as a shut-off device, the amount of cooling can be controlled either by the valve 12 or by the control valve 15. If the switching valve means are provided in a manner which includes a shut-off position, it is not necessary to use the devices 12 and 12' as shut-off devices, since the heat exchanger 5 can be decoupled from both the loops 9 and 9' in such a case by the switching valve means 22 and 23 operated together. If it should be found sufficient to control the rate of cooling by the control valve 15 and to control the rate of heating by the heater 19, and at the same time the switching valve means 22 and 23 have a shut-off position, the devices 12 and 12' can be dispensed with.

It will therefore be seen that although the invention has been described with respect to particular illustrative examples further variations and modifications are possible within the inventive concept.

We claim:

1. A climatic test chamber comprising a test room and an air-conditioning room and means for circulating air of said test room through said air-conditioning room, and further comprising:

a heat exchanger (5) in said air-conditioning room (2) for heating or cooling air of said test room (2) and of a construction suitable for operation either as an evaporator or as a condenser according to the direction of circulation of a first fluid heat transfer medium therethrough between upper and lower flow connections for said heat transfer medium which are provided for said heat exchanger (5);

first (22) and second (23) three-port, two-path switching valve means each having a port for a common path portion, passing through said heat exchanger, for said first fluid heat transfer medium, said first switching valve means (22) having its common path portion port connected to said upper flow connection of said heat exchanger, said second switching valve means (23) having its common path portion port connected to said lower flow connection of said heat exchanger and situated for accepting gravity feed of condensate from said lower flow connection of said heat exchanger (5);

said first and second valve means (22, 23) being controllable for substantially simultaneously switching their respective common path ports between respective first path ports and respective second path ports of said switching valve means for reversing the flow of said first heat transfer medium through said heat exchanger (5) and simultaneously transferring said flow from a first path (11, 12) for cooling said flow to a second path (11', 12') for heating said flow, or from said second to said first path;

a condenser (11) having a vapor inlet connected to said first path port of said first switching valve means (22), a condensate outlet connected for gravity feed of condensate to said first path port of said second switching valve means (23) and containing cooling means for condensing said vapor comprising an evaporator for a second fluid heat transfer medium connected for circulation of said second fluid heat transfer medium through a cooling system including said evaporator (13) in said condenser (11) for said first fluid heat transfer medium;

an evaporator (11') for said first fluid heat transfer medium having a condensate inlet connected for gravity feed thereto of said first medium from said second-path port of said second switching valve means (23), a vapor outlet connected for supplying vapor to said second path of said first switching valve means (22) and means (19) for heating and vaporizing said condensate, said first fluid heat transfer medium being a tempering system medium having a boiling point variable over a wide range of climate temperatures according to its pressure and said first second paths each constituting, together with said heat exchanger (5) in said air conditioning room, a system in which the pressure rises as air temperature in said test chamber increases and falls as air temperature falls in said test chamber.

2. A climatic test chamber as defined in claim 1, wherein a first control valve means (12) for controlling the cooling rate of air in said test chamber (4) produced by said heat exchanger (5) by controlling the flow of said first medium in said first path, provided for cooling said first medium, is inserted between the condensate outlet of said condenser (11) and said first path port of said second switching valve means (23) and a second control valve means (12') for controlling the heating rate of air in said test chamber (4) produced by said heat exchanger (5) by controlling the flow of said first fluid heat transfer medium in said second path, provided for heating said medium, is interposed between the vapor outlet of said evaporator (11') for said first fluid heat transfer medium and said second path port of said first switching valve means, and wherein said first path and said second path each constitute, together with said heat exchanger (5) in said air-conditioning room, a substantially closed system in which said first heat exchange medium may circulate while its condensing point temperature falls as air in said test chamber cools and its boiling point temperature rises as air in said test chamber rises.

3. A climatic test chamber as defined in claim 2, wherein second heating means (8) are provided for heating air from said air-conditioning room (2) flowing towards to said test room (4).

4. A climatic test chamber as defined in claim 3, wherein said heat exchanger comprises a plurality of parallel tubes oriented between the horizontal and an inclination of not more than 5 degrees thereto connected at first ends thereof which are not higher than the second other ends thereof through a manifold tube to said lower flow connection and opening out at said second ends thereof into a manifold duct connected to said upper flow connection of said heat exchanger.

5. A climatic test chamber as defined in claim 2, wherein said condenser (11), said evaporator (11') for said first fluid heat exchange medium, said first and second control valves (12'), said first and second switching valve means (22, 22') and said cooling system (14-167, 25) for said condenser (11), in which system said second fluid heat exchange medium circulates, are all located outside of an insulating enclosing wall containing said test room (4) and said air-conditioning room (2).

6. A climatic test chamber as defined in claim 2, wherein said evaporator 13 for said second fluid heat exchange medium for cooling of said first fluid heat exchange medium in said condenser (11) is a tube and sheet heat exchanger.

7. A climatic test chamber as defined in claim 2, wherein said evaporator 13 for said second fluid heat exchange medium for cooling of said first fluid heat exchange medium in said condenser (11) has the construction of finned tube.

8. A climatic test chamber as defined in claim 2, wherein said evaporator 13 for said second fluid heat exchange medium for cooling of said first fluid heat exchange medium in said condenser (11) is in the form of a serpentine tube.

9. A climatic test chamber as defined in claim 1, wherein said first heat exchange medium is a halogen-substituted hydrocarbon containing at least one atom of fluorine per molecule.

10. A climatic test chamber as defined in claim 1, wherein said heating means (19) of said evaporator (11') for said first fluid heat exchange medium is an electrical resistance heater.

* * * * *